US007782460B2

(12) United States Patent
DiFoggio et al.

(10) Patent No.: US 7,782,460 B2
(45) Date of Patent: Aug. 24, 2010

(54) LASER DIODE ARRAY DOWNHOLE SPECTROMETER

(75) Inventors: Rocco DiFoggio, Houston, TX (US); Sebastian Csutak, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 164 days.

(21) Appl. No.: 11/837,753

(22) Filed: Aug. 13, 2007

(65) Prior Publication Data

US 2008/0165356 A1 Jul. 10, 2008

Related U.S. Application Data

(63) Continuation-in-part of application No. 11/592,887, filed on Nov. 3, 2006, which is a continuation-in-part of application No. 10/836,675, filed on Apr. 30, 2004, now Pat. No. 7,196,786.

(60) Provisional application No. 60/468,372, filed on May 6, 2003.

(51) Int. Cl.
*G01N 21/25* (2006.01)
*G01N 21/00* (2006.01)
*G01J 3/42* (2006.01)
*G01J 3/427* (2006.01)
*G01J 3/433* (2006.01)
*G01J 3/447* (2006.01)
*G01V 5/08* (2006.01)
*G01V 5/00* (2006.01)
*G01V 5/04* (2006.01)

(52) U.S. Cl. .............. 356/409; 356/319; 356/323; 356/326; 356/436; 250/263; 250/269.1

(58) Field of Classification Search .......... None
See application file for complete search history.

(56) References Cited

U.S. PATENT DOCUMENTS

| | | | |
|---|---|---|---|
| 2,431,487 A | | 11/1947 | Larsen et al. |
| 4,802,761 A | | 2/1989 | Bowen et al. |
| 4,937,448 A | | 6/1990 | Mantz et al. |
| 4,994,671 A | * | 2/1991 | Safinya et al. ............. 250/255 |
| 5,166,747 A | | 11/1992 | Schroeder et al. |
| 5,167,149 A | * | 12/1992 | Mullins et al. ............ 73/152.42 |
| 5,201,220 A | * | 4/1993 | Mullins et al. ............ 73/152.42 |

(Continued)

OTHER PUBLICATIONS

Bamford, Douglas et al., "Widely-Tunable Rapid-Scanning Mid-IR Laser Spectrometer for Industrial Gas Process Stream Analysis," Laser Applications to Chemical, Security and Environmental Analysis 2006, Feb. 5-9, 2006, Incline Village, Nevada.

(Continued)

*Primary Examiner*—Tarifur Chowdhury
*Assistant Examiner*—Gordon J Stock, Jr.
(74) *Attorney, Agent, or Firm*—Cantor Colburn LLP (57) ABSTRACT

Apparatus and method for downhole formation testing using a spectrometer includes a carrier conveyable into a well borehole that traverses a subterranean formation of interest, a plurality of semiconductor light sources disposed on the carrier, a fluid sample cell that receives light emitted from the plurality of semiconductor light sources, and at least one photodetector that detects light emitted from the plurality of semiconductor light sources and after the light interacts with a fluid in the fluid sample cell.

25 Claims, 5 Drawing Sheets

U.S. PATENT DOCUMENTS

| | | | |
|---|---|---|---|
| 5,317,156 A | | 5/1994 | Cooper et al. |
| 5,331,156 A | | 7/1994 | Hines et al. |
| 5,331,409 A | * | 7/1994 | Thurtell et al. ............... 356/437 |
| 5,475,221 A | * | 12/1995 | Wang .................... 250/339.07 |
| 5,550,375 A | * | 8/1996 | Peters et al. ................. 250/343 |
| 5,781,284 A | | 7/1998 | Infante |
| 5,808,779 A | * | 9/1998 | Weis .......................... 359/290 |
| 5,821,536 A | * | 10/1998 | Pettit ....................... 250/339.1 |
| 6,064,488 A | | 5/2000 | Brand et al. |
| 6,353,225 B1 | | 3/2002 | Strzoda et al. |
| 6,437,326 B1 | | 8/2002 | Yamate et al. |
| 6,590,647 B2 | | 7/2003 | Stephenson |
| 6,608,677 B1 | | 8/2003 | Ray et al. |
| 6,670,605 B1 | | 12/2003 | Storm, Jr. et al. |
| 6,678,050 B2 | | 1/2004 | Pope et al. |
| 6,683,681 B2 | | 1/2004 | DiFoggio et al. |
| 6,729,400 B2 | | 5/2004 | Mullins et al. |
| 6,798,518 B2 | * | 9/2004 | DiFoggio et al. ............ 356/416 |
| 6,888,127 B2 | | 5/2005 | Jones et al. |
| 6,901,101 B2 | * | 5/2005 | Frick ........................... 372/92 |
| 6,967,322 B2 | | 11/2005 | Jones et al. |
| 6,997,055 B2 | | 2/2006 | DiFoggio |
| 7,028,773 B2 | | 4/2006 | Fujisawa et al. |
| 7,034,302 B2 | * | 4/2006 | Davidson et al. ......... 250/339.1 |
| 7,084,392 B2 | | 8/2006 | DiFoggio et al. |
| 7,095,012 B2 | | 8/2006 | Fujisawa et al. |
| 7,173,239 B2 | | 2/2007 | DiFoggio |
| 7,196,786 B2 | | 3/2007 | DiFoggio |
| 7,197,195 B2 | | 3/2007 | DiFoggio et al. |
| 7,214,933 B2 | | 5/2007 | DiFoggio et al. |
| 7,279,678 B2 | | 10/2007 | Andrews et al. |
| 7,284,903 B2 | * | 10/2007 | Hartog ....................... 374/130 |
| 7,333,190 B1 | | 2/2008 | Pendell-Jones et al. |
| 7,428,434 B2 | * | 9/2008 | Tromberg et al. ............ 600/476 |
| 7,609,380 B2 | * | 10/2009 | Vannuffelen et al. ........ 356/326 |
| 2002/0043620 A1 | * | 4/2002 | Tchakarov et al. ....... 250/269.1 |
| 2002/0074489 A1 | | 6/2002 | Mullins et al. |
| 2003/0033866 A1 | | 2/2003 | Diakonov et al. |
| 2003/0048450 A1 | * | 3/2003 | Pope et al. ................... 356/435 |
| 2003/0049858 A1 | | 3/2003 | Golden et al. |
| 2003/0134426 A1 | | 7/2003 | Jiang et al. |
| 2004/0164237 A1 | | 8/2004 | Jones et al. |
| 2004/0218176 A1 | | 11/2004 | Shammal et al. |
| 2005/0103980 A1 | | 5/2005 | Schultz et al. |
| 2006/0115204 A1 | | 6/2006 | Marsh et al. |
| 2006/0139646 A1 | | 6/2006 | DiFoggio |
| 2006/0146337 A1 | | 7/2006 | Hartog |
| 2006/0209291 A1 | | 9/2006 | Yamate et al. |
| 2006/0239330 A1 | | 10/2006 | Yamate et al. |
| 2007/0013911 A1 | | 1/2007 | DiFoggio |
| 2007/0062696 A1 | | 3/2007 | Wilson et al. |
| 2007/0068242 A1 | | 3/2007 | DiFoggio |
| 2007/0171412 A1 | | 7/2007 | Vannuffelen et al. |

OTHER PUBLICATIONS

Li, Hejie et al., "Extension of wavelength-modulation spectroscopy to large modulation depth for diode laser absorption measurements in high-pressure gases," Applied Optics, Feb. 10, 2006, vol. 45, No. 5; pp. 1052-1061.

Voronov, Yu. Yu. et al., "Absorption Spectra of Gasolines in the Region," Journal of Applied Spectroscopy, 2003, vol. 70, No. 4; pp. 628-631.

International Search Report, Date of Mailing Oct. 22, 2008, for PCT/US2008/072477 filed on Aug. 7, 2008.

\* cited by examiner

LASER DIODE ARRAY DOWNHOLE SPECTROMETER

CROSS-REFERENCE TO RELATED APPLICATIONS

The present application is a continuation-in-part of U.S. patent application Ser. No. 11/592,887 for "APPARATUS AND METHOD FOR ESTIMATING FILTRATE CONTAMINATION IN A FORMATION FLUID," filed on Nov. 3, 2006, which is a continuation-in-part of U.S. patent application Ser. No. 10/836,675 for "METHOD AND APPARATUS FOR A TUNABLE DIODE LASER SPECTROMETER FOR ANALYSIS OF HYDROCARBON SAMPLES" filed on Apr. 30, 2004, now U.S. Pat. No. 7,196,786, which relates to and claim priority from U.S. Provisional application Ser. No. 60/468,372 of the same title filed on May 6, 2003, the entire contents of each of these prior applications is hereby incorporated herein by reference.

BACKGROUND

1. Technical Field

The present disclosure generally relates to well bore tools and in particular to apparatus and methods for downhole spectrometry.

2. Background Information

Oil and gas wells have been drilled at depths ranging from a few thousand feet to as deep as 5 miles. Wireline and drilling tools often incorporate various sensors, instruments and control devices in order to carry out any number of downhole operations. These operations may include formation testing, fluid analysis, and tool monitoring and control.

The environment in these wells present many challenges to maintain the tools used at depth due to vibration, harsh chemicals and temperature. Temperature in downhole tool applications presents a unique problem to these tools. High downhole temperatures may reach as high as 390 degrees F. or more, and sensitive electronic equipment must be cooled in order to work in the environment. An added problem is that space in the carrier assembly is usually limited to a few inches in diameter.

High resolution spectrometers, 1-2 nm bandpass for each optical channel for example, are typically completely located at a surface location with fluid samples being transported to the surface for analysis or they use optic fibers to carry light from the surface to a downhole sample. Some wireline tools use downhole spectrometers that analyze fluids in the downhole environment but generally at comparatively low spectral resolution of about 20-30 nm bandpass for each optical channel.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

Disclosed is a downhole spectrometer apparatus for formation testing. The apparatus includes a carrier conveyable into a well borehole that traverses a subterranean formation of interest, a plurality of semiconductor light sources disposed on the carrier, a fluid sample cell that receives light emitted from the plurality of semiconductor light sources, and at least one photodetector that detects light emitted from the plurality of semiconductor light sources and after the light interacts with a fluid in the fluid sample cell.

In another aspect, a method for testing a formation using a downhole spectrometer includes conveying a carrier into a well borehole that traverses a subterranean formation of interest, emitting light from a plurality of semiconductor light sources disposed on the carrier, receiving the light at a fluid sample cell, and detecting the light emitted from the plurality of semiconductor light sources and after the light interacts with a fluid in the fluid sample cell using at least one photodetector.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DESCRIPTION OF EXEMPLARY EMBODIMENTS

The present disclosure uses terms, the meaning of which terms will aid in providing an understanding of the discussion herein. As used herein, high temperature refers to a range of temperatures typically experienced in oil production well boreholes. For the purposes of the present disclosure, high temperature and downhole temperature include a range of temperatures from about 100° C. to about 200° C. (about 212° F. to about 390° F.).

Figure 1:
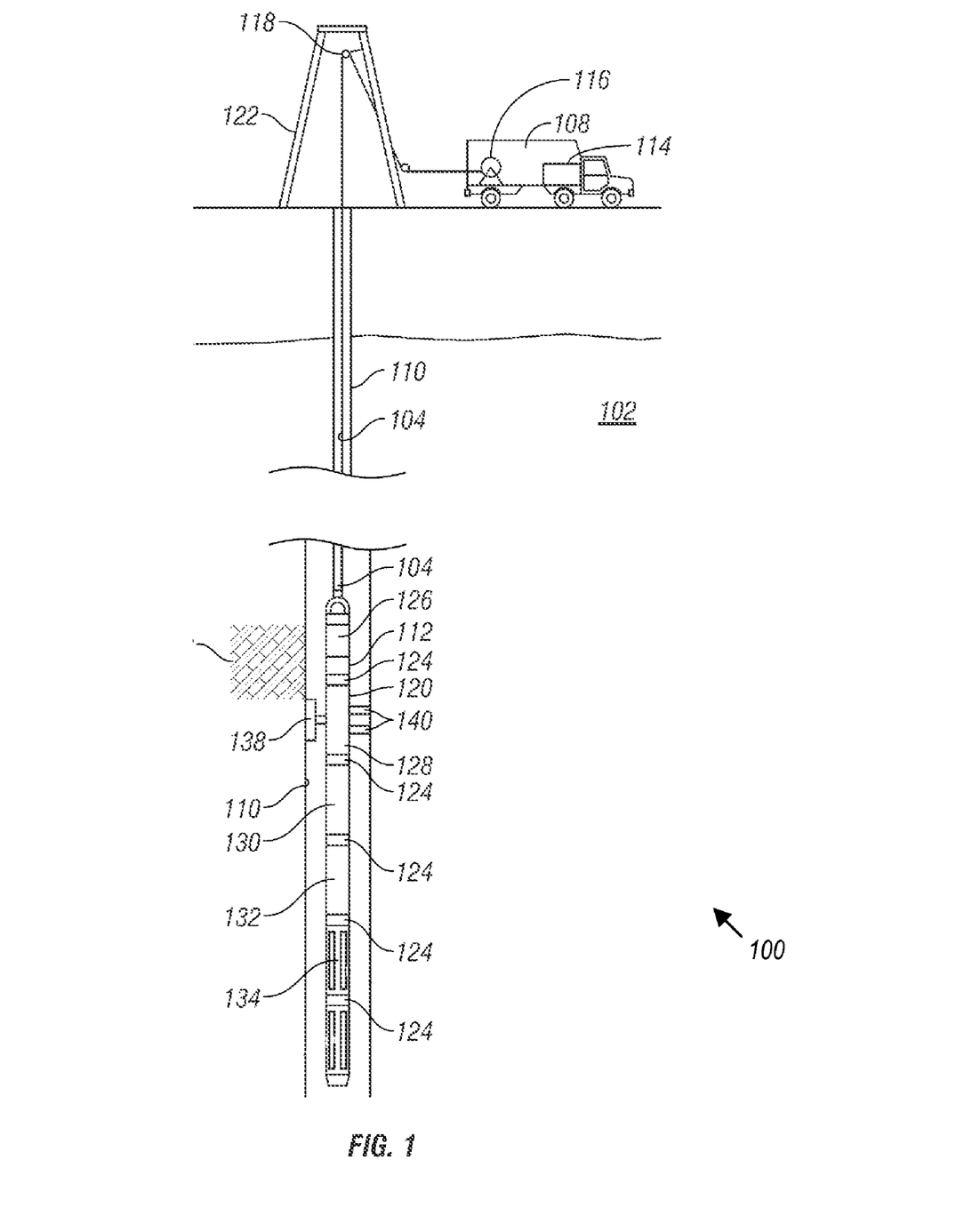
FIG. 1 is an exemplary wireline system according to several embodiments of the disclosure.

FIG. 1 schematically illustrates a non-limiting example of a wireline apparatus 100 according to several disclosed embodiments. In the example shown, a well borehole 112 traverses several subterranean formations 102. The well borehole 112 will typically be filled or at least partially filled with a fluid mixture of including various gases, water, drilling fluid, and formation fluids that are indigenous to the subterranean formations penetrated by the well borehole. Such fluid mixtures are referred herein to as "well borehole fluids". The terms "connate fluid" and "natural fluid", as used herein, refer to fluids naturally existing in or extracted from the subterranean formations 102 and exclusive of any substantial mixture or contamination by fluids not naturally present in the formation, such as drilling fluid.

A formation evaluation tool 120 is conveyed in the well borehole 110 using a wire line 104. Wire line deployment and retrieval may be performed by a powered winch carried by a service truck 108, for example. The wireline 104 typically is an armored cable that carries data and power conductors for providing power to the formation evaluation tool 120 and to provide two-way data communication between a tool processor 112 and a controller 114 that may be carried by the service truck 108. The wireline 104 typically is carried from a spool 116 over a pulley 118 supported by a derrick 122. The spool 116 may be carried by the truck 108 as shown for on-land operations, by an offshore rig for underwater operations or by any other suitable mobile or fixed supporting structure. The controller 114 may include a processor, such as within a computer or a microprocessor, data storage devices, such as solid state memory and magnetic tapes, peripherals, such as data input devices and display devices, and other circuitry for controlling and processing data received from the tool 120. The surface controller 114 may further include one or more computer programs embedded in a computer-readable medium accessible to the processor in the controller 114 for executing instructions contained in the computer programs to perform the various methods and functions associated with the processing of the data from the tool 120.

The formation evaluation tool 120 lower portion may include an assembly of several tool segments that are joined end-to-end by threaded sleeves or mutual compression unions 124. An assembly of tool segments appropriate for the present invention may include a hydraulic, electrical or electro-mechanical power unit 126 and a formation fluid extractor 128. A large displacement volume motor/pump unit 130 may be provided below the extractor 128 for line purging. A similar motor/pump unit 132 having a smaller displacement volume may be included in the tool in a suitable location, such as below the large volume pump, for quantitatively monitoring fluid received by the tool 120. One or more sample tank magazine sections 134 may be included for retaining fluid samples from the small volume pump 132. Each magazine section 126 may have several fluid sample tanks 136.

The formation fluid extractor 128 comprises an extensible suction probe 138 that is opposed by bore wall feet 140. Both, the suction probe 138 and the opposing feet 140 may be hydraulically or electro-mechanically extensible to firmly engage the well borehole wall. Construction and operational details of a suitable fluid extraction tool 128 are more described by U.S. Pat. No. 5,303,775, the specification of which is incorporated herein by reference.

Figure 2:
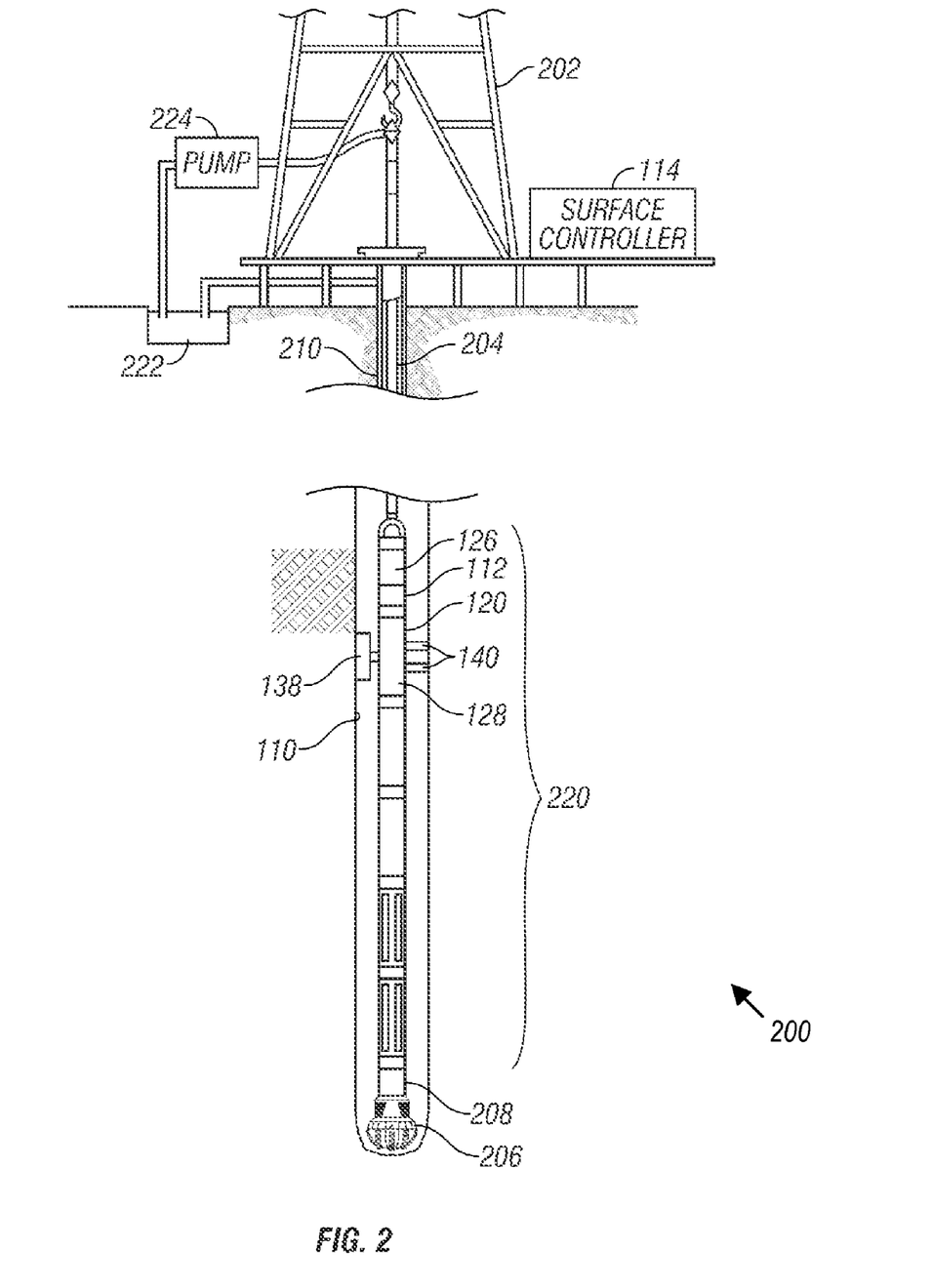
FIG. 2 illustrates a non-limiting example of a while-drilling system according to the disclosure.

FIG. 2 schematically illustrates a non-limiting example of a drilling system 200 in a measurement-while-drilling (MWD) arrangement according to one embodiment of the disclosure. A derrick 202 supports a drill string 204, which may be a coiled tube or drill pipe. The drill string 204 may carry a bottom hole assembly (BHA) 220 and a drill bit 206 at a distal end of the drill string 204 for drilling a borehole 110 through earth formations.

Drilling operations according to several embodiments may include pumping drilling fluid or "mud" from a mud pit 222, and using a circulation system 224, circulating the mud through an inner bore of the drill string 204. The mud exits the drill string 204 at the drill bit 206 and returns to the surface through an annular space between the drill string 204 and inner wall of the borehole 110. The drilling fluid is designed to provide the hydrostatic pressure that is greater than the formation pressure to avoid blowouts. The pressurized drilling fluid may further be used to drive a drilling motor 208 and may provide lubrication to various elements of the drill string 204.

In the on-limiting embodiment of FIG. 2, the BHA 220 includes a formation evaluation tool 120 substantially similar to the tool 120 described above and shown in FIG. 1.

The while-drilling tool 120 may carry a fluid extractor 128 including a probe 138 and opposing feet 140. In several embodiments to be described in further detail later, the tool 120 includes a downhole spectrometer. The spectrometer may be used in either the while-drilling embodiments or in the wireline embodiments.

Figure 3:
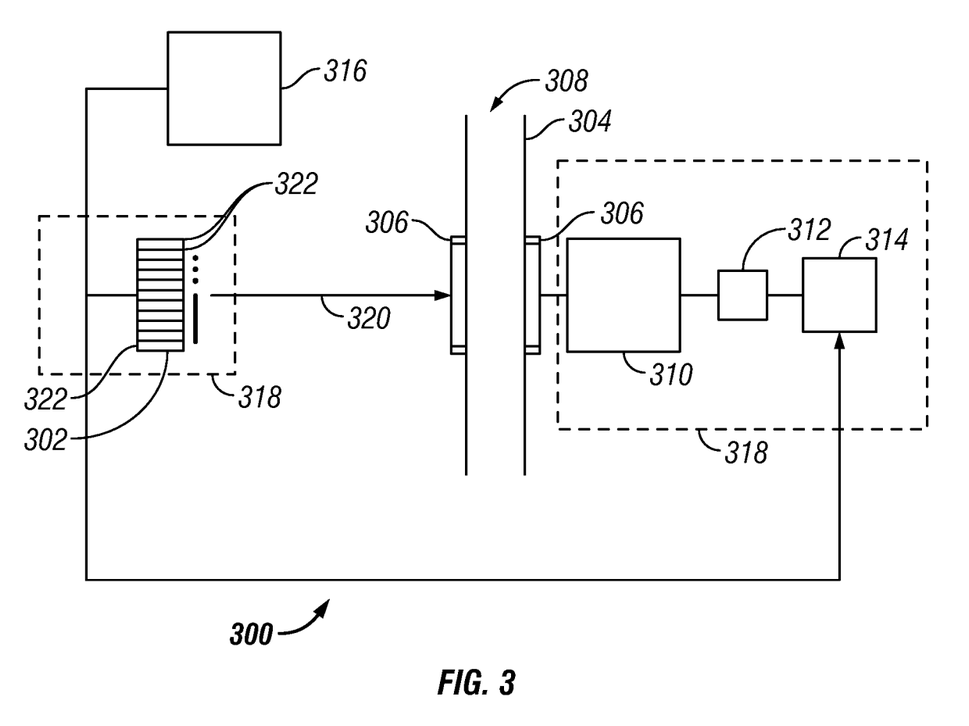
FIG. 3 is a non-limiting example of a downhole spectrometer that may be us with systems such as those depicted in FIGS. 1 and 2.

FIG. 3 schematically illustrates a non-limiting example of a downhole spectrometer 300 according to the disclosure. The downhole spectrometer 300 may be incorporated into any of several wireline tools, including the formation evaluation tool 120 described above and shown in FIG. 1. In other embodiments, the downhole spectrometer may be incorporated into a while-drilling tool, such as the tool 120 or BHA 220 described above and shown in FIG. 2. The downhole spectrometer 300 includes multiple optical channels with each optical channel having a light source.

The downhole spectrometer 300 in the example shown includes an array 302 of individual light sources 322. The array 302 of light sources 322 emits light toward a formation fluid cell 304 via an optical path 320. The optical path may be any path that provides optical transmission. In one embodiment, the optical path 320 may include an air gap. In another embodiment, the optical path 320 includes an optical fiber.

The fluid cell 304 includes at least one window 306 for receiving the emitted light, so that the light may interact with fluid 308 within the cell 304. Several configurations of sample cells and windows may be used in other embodiments without departing from the scope of the present disclosure. For example, to measure optical transmittance through a cell, one could use a pair of windows. Transflectance measurements may be conducted using a single window with a mirror behind the window and having the fluid sample between the mirror and window. Attenuated reflectance measurements may be conducted using a single window in contact with the fluid sample. Raman scattering and fluorescence measurements may be conducted using a single window and collecting the resulting light on the same side of the window as the source light. In another example, light may be collected through a second window for Raman scattering and fluorescence measurements. Depending on the opacity of the sample, the second window could collect the resulting light at 90 degrees from the direction of the source light.

Continuing with the example of FIG. 3, a photodetector 310 receives the light after the light interacts with the fluid 306. The photodetector 310, which may be a single broadband photodetector, is responsive to light emitted from the array and provides an output signal indicative of the light received at the photodetector 310. In some cases, the photodetector output signal is an analog electrical signal. An analog-to-digital converter 312 may be used to convert the photodetector output signal into a digital signal that is received by a processor that is part of a modulator 314, 316 that may be part of a controller having a processor. The light emitted from the array 302 may be modulated by a processor within the same controller that receives the photodetector output or by a separate modulator. In the example shown, one modulator/controller 314 is coupled to the photodetector 310 and a second modulator/controller 316 is coupled to the array 302. These controllers may be implemented as a single controller without departing from the scope of the disclosure. In other embodiments, the controller or controllers 314, 316 may be located at the surface of the well borehole. In wireline embodiments, communication may be accomplished via the wireline cable. In while-drilling embodiments, communication may be accomplished via wired pipe, acoustic pipe communication or by mud-pulse telemetry. In wireline embodiments disclosed herein, the array 302 may be located at a well borehole surface location and the optical fiber 320 may extend from the surface location to the downhole tool using the wireline cable as a support. In this surface array embodiment, modulation spectroscopy disclosed herein may be accomplished by controlling the array 302 at the surface.

In one embodiment, the array 302 may include one or more light-emitting semiconductors used as the individual light sources 322. For example, the array 300 may include laser diodes. The laser diodes may all be coupled to a single optical fiber 320, and light from that fiber would interact with the fluid 308 (through transmission or through attenuated reflection) and afterwards be detected by the photodetector 310. In other embodiments, the downhole spectrometer 300 may include arrayed light sources 322 that are not all lasers, i.e. optical channels that have a wider bandpass (less resolution) than a laser. In these embodiments, an array of light-emitting diodes (LED) may be used.

The light emitted by each light source 322 in the array 302 is controlled (i.e. modulated) by the controller 314, 316. The processor 314, 316 that receives the detector 310 output signal may also receive a signal from the controller 314, 316 modulating the array 302, where the modulator signal is indicative of which individual light source 322 within the array 302 emitted the light at a particular point in time or of a particular frequency or of a particular wavelength or of a particular intensity. When each light source is modulated and/or selected to emit a predetermined wavelength, then no filtering is required for distinguishing spectra over the wide bandwidth of the array 302.

Modulation may be conducted in any number of useful ways according to the disclosure. The simplest approach is to turn on each light source one at a time to collect the spectra associated with each light source in serial fashion. For much faster collection of spectra, in one embodiment, each of the different-wavelength light sources is modulated at a different electrical frequency but ultimately their light is detected by a single photodetector. The photodetector output signal is conveyed to the processor or other electrical filter, and the photodetector output signal is electrically filtered to determine the spectral contribution from each light source. In another embodiment, to achieve faster collection of spectra, some subset (for example, half) of the light sources are turned on simultaneously and the photodetector signal is recorded. Then, some other comparably sized subset of the light sources is turned on, and so on. This approach is analogous to a Hadamard mask. After a series of such measurements, one has effectively generated N equations in N unknowns and can solve for the individual contribution of each light source even though no light source was ever turned on alone.

The downhole spectrometer 300 according to one embodiment may include an array 302 of laser diodes 322 having different wavelengths and a single photodetector 310. Using a single photodetector assumes that this photodetector is responsive to the range of wavelengths emitted by the laser diode array 302. Photodetectors typically experience drift with respect to another as temperature increases, meaning that the response characteristics of each photodetector is unique when subjected to temperature fluctuations. Using a single photodetector eliminates the need to account for differences in how one photodetector drifts with respect to others. A common optical measurement is absorbance, which is the base ten logarithm of the ratio of light entering a fluid sample to light exiting the fluid sample. From experience, we found that, although a photodetector's response is diminished at elevated temperatures and its baseline drifts, its response still varies linearly with incident light intensity. Thus, using a single photodetector when making a ratio measurement such as absorbance, especially at high temperatures, avoids errors due to drift. Because of its simplicity, the spectrometer 300 according to the disclosure has a higher reliability and is robust.

Each laser 322 in the array 302 can be configured or selected to emit a light having a wavelength corresponding to a different optical channel of the spectrometer 300. In one embodiment, modulating the laser diodes includes turning each diode on individually and sequentially using the controller 314, 316 so that each laser 322 in the array 302 emits a specific wavelength of light through the fluid cell 304 at a different time. An optical absorption spectrum could then be generated by comparing, for each wavelength, the response when the cell is filled with fluid to the response when the cell is empty.

Cooling one or more of these downhole components may be accomplished using a cooling device 318. The cooling device 318 used may be any number of devices, examples of which include thermal-electric, thermo-tunneling, sorption cooling, evaporators, and Dewar. Cooling is optional where components selected are compatible with the downhole temperature environment. Cooling may be applied where a component operating temperature is lower than the downhole environment and/or were cooling may enhance performance of the component. In several embodiments, the array 302 is compatible with the downhole temperature environment. Cooling in some cases could improve photodetector signal-to-noise ratio and increase laser brightness. Maintaining the lasers at a constant temperature could provide wavelength stability. In one embodiment, the array is maintained at a substantially constant temperature, and the wavelength of each laser diode may be modulated by rapidly changing its temperature over a small temperature range. This would most easily be done by rapidly changing the current through the laser or by changing electrical current supplied to auxiliary resistive heaters in thermal contact with each light source. In another embodiment the wavelength is modulated by using an external cavity. Alternatively, each laser diode's wavelength could be slightly modulated by slightly modulating its temperature, which is done most easily by modulating the current through it.

In another embodiment, the wavelength of each laser may be modulated at a different frequency, which would save time through the multiplexing advantage associated with measuring all wavelengths simultaneously with a single photodetector. Then, the output of the photodetector could be filtered (digitally or in hardware) to recover that portion of the photodetector response that is due to any particular laser.

In several embodiments, the modulation frequencies could be "relatively prime" (i.e. have no or very few common factors other than unity within the wavelength spectrum of interest) to avoid aliasing effects. Any set of prime numbers is a set of relatively prime numbers. For example, for a 10-wavelength spectrometer, the ten modulation frequencies could be the prime numbers 11 Hz, 13 Hz, 17 Hz, 19 Hz, 23 Hz, 29 Hz, 31 Hz, 37 Hz, 41 Hz, and 43 Hz. Other set of numbers having non-prime numbers may also be considered sets of relatively prime numbers within the scope of the disclosure. The photodiode's electrical signal may be electrically filtered to separate and extract the signal associated with each of the different-wavelength light sources.

In embodiments utilizing wavelength modulation spectroscopy, response comparison using an empty cell is optional, because the response changes due to input light modulation may be used alone and with a response average value in order to calculate a first derivative of the optical absorption spectrum. Photodetector response typically drifts with temperature, so the difference in photodetector response between a dark period (light off) and a period during which one of the lasers is on may be used for checking calibration. In this manner, each laser could be turned on, a reading taken using the photodetector, and then the laser can be turned off and another reading taken using the photodetector. Taking the difference of the two readings would remove any spurious photodetector response drift with temperature. In one embodiment, the on-off cycles may be rapid enough to simply generate, by analog circuits, a root-mean-square value of this square-wave signal. By using a single photodetector, inter-calibration issues associated with using multiple photodetectors can be avoided. Inter-calibration issues can be troublesome, because any two photodetectors typically will have different drift characteristics at elevated temperatures. Furthermore, it is less complicated to cool a single photodetector than it is to cool an array of photodetectors. Moreover, downhole electrical power constraints are easier to manage with fewer detectors. Cooling a photodetector by about 30 degrees Celsius below downhole temperature can greatly improve photodetector performance.

Semiconductor light sources 322 may be cooled using a cooling device 318. The cooling device may be any cooling device useful in a downhole environment; several non-limiting examples include thermoelectric cooling, thermo-tunneling cooling, and sorption cooling.

In other embodiments, the light source 322 may include high-temperature semiconductor light sources that operate effectively in the downhole temperature environment without the need for cooling devices. Examples of such downhole devices are described in co-pending U.S. patent application for "High Temperature Downhole Tool" filed concurrently with the present application on Aug. 13, 2007, Ser. No. 11/837,692, and which application is incorporated herein by reference and is assigned to the assignee of the present application. Some of the more pertinent discussion from the co-pending application is discussed below with reference to FIGS. 6 and 7.

Figure 4:
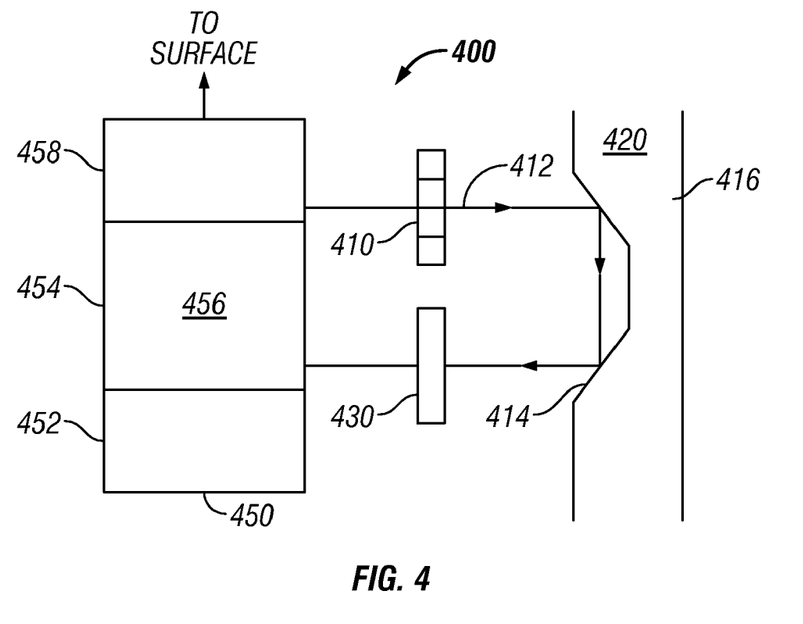
FIGS. 4 and 5 illustrate downhole Raman spectrometer examples according to several embodiments of the disclosure.

Turning now to FIG. 4, a schematic diagram illustrates a Raman spectrometer 400 that may be used downhole for analyzing fluid withdrawn from a formation. The Raman spectrometer 400 includes a UV laser array 410 that induces or pumps UV light 412 into a fluid 420 through a window 414 made into a wall of a fluid chamber 416. The light path from the array 410 to the window 414 may be an optical fiber such as the fiber 320 described above and shown in FIG. 3. The UV laser array 410 of this example includes multiple lasers producing UV light within a relatively narrow wavelength band. Alternatively, the UV laser array 410 may produce multiple monochromatic (single wavelength) UV light from each laser. The light 412 interacts with the fluid 420 and a portion of the light is reflected back to a detector 430. The detector produces a signal responsive to the light, which signal is received by a controller 450 for analysis. The controller 450 may further be used as a modulator for the array 410 to modulate the light emitted from the array 410.

An advantage of a UV laser diode such as one made from GaN is that, because of its wide bandgap, the laser can operate better at high temperature in that there is less dimming and less chance of lasing cessation than when using a narrower bandgap laser at the high temperatures encountered downhole. Here, wide bandgap refers to bandgap energies greater than approximately 1.24 electron volts corresponding to short wavelengths. Here, short wavelengths refer to wavelengths less than approximately 1000 nm.

In another embodiment, the array 410 includes several UV lasers and the light emitted from at least two of the UV or other short wavelength lasers in the laser array 410 is combined and passed through a nonlinear optical medium such as an optic fiber 320 or other non-linear medium to produce four-wave mixing. These four waves include the two original wavelengths, a wavelength corresponding to the sum of their energies and a wavelength corresponding to the difference of their energies. This difference energy can be small enough to correspond to infrared wavelengths. In this manner infrared wavelengths may be generated using two wide-bandgap laser diodes instead of a single infrared laser diode where the small bandgap of the infrared diode does not provide adequate performance in a high temperature environment without additional cooling. Using four-wave mixing as described above provides infrared and near-infrared spectroscopy for chemical identification using a pair of temperature-resistant wide bandgap laser diodes.

Raman spectroscopy is based on the Raman Effect, which is the inelastic scattering of photons by molecules. In Raman scattering, the energies of the incident or pumped photons and the scattered photons are different. The energy of Raman scattered radiation can be less than the energy of incident radiation and have wavelengths longer than the incident photons (Stokes Lines) or the energy of the scattered radiation can be greater than the energies of the incident photons (anti-Stokes Lines) and have wavelengths shorter than the incident photons. Raman spectroscopy analyzes these Stokes and anti-Stokes lines. The spectral separation between the optical pump wavelength and the Raman scattered wavelengths form a spectral signature of the compound being analyzed. Oil-based mud filtrate often has a distinct spectral signature due to the presence of olefins and esters, which do not naturally occur in crude oils. In this way, Raman spectroscopy can be used to calculate the percentage of oil based mud filtrate contamination of crude oil samples as they are being collected downhole. One can continue withdrawing and discarding oil removed from the downhole formation until the contamination falls below a desired level and then divert the sample being withdrawn into a sample collection tank. However, fluorescence from aromatics in the fluid sample, often has much higher intensity, and can interfere or obscure certain Raman signals. By using source lights having a wavelength around 250 nm or less, the Raman spectrum is completed at wavelengths shorter than those at which fluorescence begins and, therefore, interference is eliminated.

Thus, in one aspect, the laser array 410 produces UV light at wavelengths near or below (shorter than) 250 nm. The detector 430 may be any detector that can detect spectra of the Raman scatters corresponding to the light emitted by the laser array 410.

The light detected by the detector 430 passes to a controller 450. The controller may include a processor 452, and memory for storing data 454 and computer programs 456. The controller 450 receives and processes the signals received from the detector 430. In one aspect, the controller 450 may analyze or estimate the detected light and transmit a spectrum of the Raman scattered light to a surface controller using a transmitter 458. In one aspect, the controller 450 may analyze or estimate one or more properties or characteristics of the fluid downhole and transmit the results of the estimation to a surface controller using the transmitter 458. In another aspect, the controller 450 may process the signals received from the detector 430 to an extent and telemeter the processed data to a surface controller for producing a spectrum and for providing an in-situ estimate of a property of the fluid, including the contamination level of the mud in the formation fluid.

Figure 5:
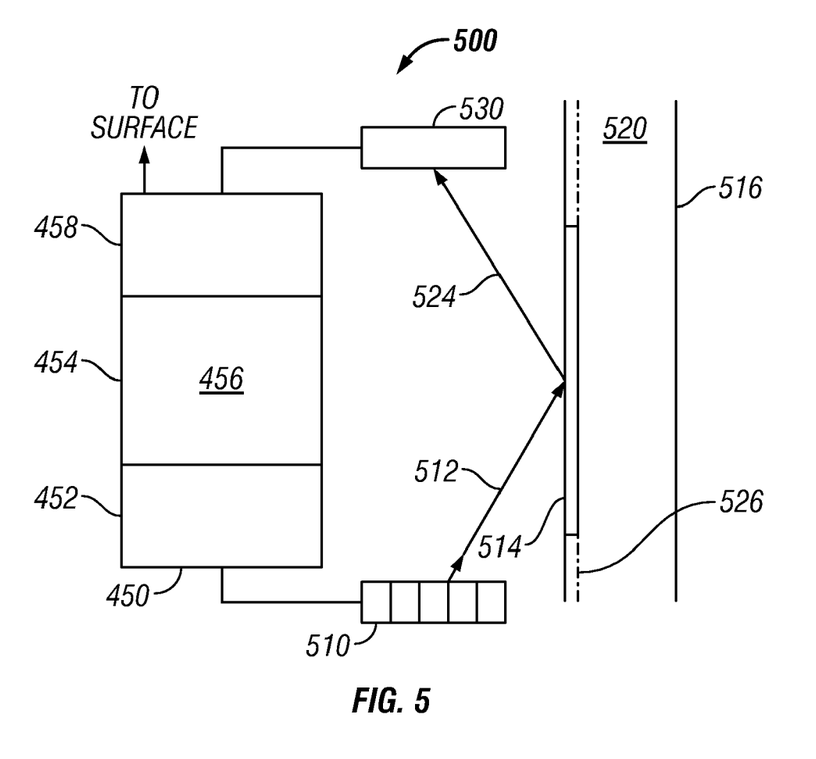

FIG. 5 is a non-limiting schematic diagram showing a portion of a surface-enhanced Raman spectrometer 500 for estimating a property of a fluid according to one embodiment of the disclosure. The exemplary spectrometer 500 shown includes a chamber 516 for holding a fluid 520 to be analyzed. The fluid 520 may be stationary or it may be passing through the chamber 516. The chamber 516 includes a window 514 for allowing light to pass to the fluid 520. The spectrometer 500 includes a laser array 510 that emits light 512. Each laser in the array 510 emits a desired wavelength or band of wavelengths. A controller 450, similar to the controller 450 described above and shown in FIG. 4, controls the operation of the laser array 510 to modulate the lasers of the array. The light path from the array 510 to the window 514 may be an optical fiber such as the fiber 320 described above and shown in FIG. 3. The incident light 512 enters the chamber 516 through the window 514 at a selected angle. The Raman scattered light 524 from the fluid 520 leaves the window 514. A detector 530, similar to the detector 430 (FIG. 4), detects the Raman spectra. A processor 452 receives the signals from the detector 530 and processes the signals to estimate a property of the fluid 520. The controller 450 may further include memory 454 and programs 456 for storing information and for controlling the tool. Likewise, a transmitter 458 may be used to communication with surface-located components.

Fluorescence can interfere with the Raman signals, so to increase the intensity of the Raman signal, an inside surface of the chamber 516 including the inside surface of the window 514 may be coated with conductive particles 526. The conductive particles 526 may be placed in the form of scattered metallic particles, a lattice type structure, or in any other suitable form that will enhance the Raman scattered light. The conductive particles can enhance the Raman Effect due to Plasmon resonance, which consists of energy exchange between the Raman signals and a surface wave that exists in a conductive layer, such as the layer of particles 526. The spectrometer 500 may be used downhole for in-situ analysis of a fluid, such as the fluid withdrawn from a formation or at the surface, to estimate one or more properties or characteristics of the fluid.

Figure 6:
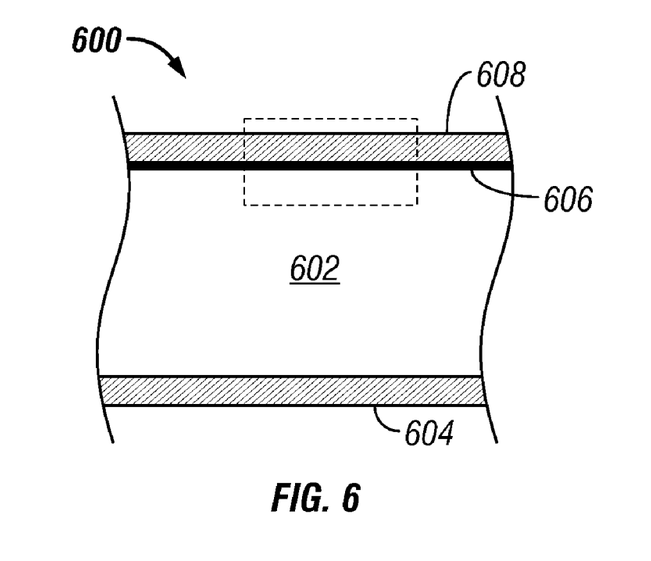
FIGS. 6 and 7 illustrate examples of high-temperature semiconductor devices that may be used in one or more of the several disclosed embodiments.
Figure 7:
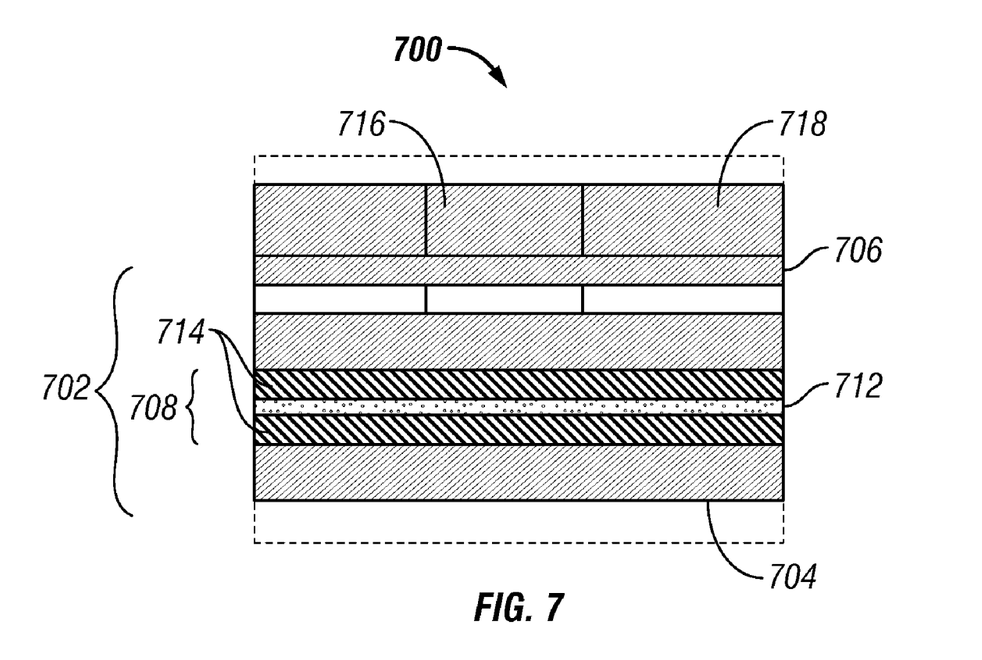

FIGS. 6 and 7 illustrate high-temperature semiconductor devices that may be used in one or more of the several embodiments discussed above and shown in FIGS. 1-5. Referring now to FIG. 6, a cross section view of an exemplary high-gain semiconductor device 600 that may be used in the several embodiments of the disclosure is shown. As used herein, the term high-gain means that the ratio of output over input that is at least higher than unity. Depending on the type of semiconductor device, gain may refer to any output/input ratio. Non-limiting examples include voltage, current, power and light (optic gain). The high-gain semiconductor device 600 includes a substrate 602 disposed on a bottom electrode 604. A high-gain media 606 is disposed on the substrate 602 and a top electrode 608 is disposed on the high-gain region 606. The terms top and bottom are merely references with respect to the non-limiting example shown in FIG. 6, and any other electrode position and/or orientation is within the scope of the disclosure. The high-gain media semiconductor 600 may be configured for any application where a high-gain region 606 is desirable, and application where more than one junction and more than two electrodes are desired are within the scope of the disclosure. In several non-limiting examples, the semiconductor device may be a diode, a transistor, a field effect transistor (FET), a laser diode or any other useful semiconductor device using a high-gain media.

The substrate 602 and high-gain media 606 of the present disclosure are selected and layered with respect to temperature that allows use with the temperature extremes of the well borehole environment. In several embodiments, speed and bandwidth may be lowered by the selection of semiconductor materials and/or dimensions. For example, thicker layering of the high-gain media materials and substrate will increase temperature tolerance and may decrease device speed and bandwidth.

In several embodiments, the high-temperature high-gain media semiconductor device 600 may be used in any number of sensor, communication, switching, amplification and information handling applications. In one non-limiting embodiment, the semiconductor 600 may be laser device that may be used in a downhole tool. In the instance of a semiconductor laser example, the laser device is a semiconductor laser where the high-gain media 606 will include an optical region sandwiched between the substrate 602 and the top electrode 608.

FIG. 7 shows a cross section of the high-gain semiconductor of FIG. 6 in more detail and where the semiconductor is configured as a laser device 700. In this example, the laser device 700 includes an optical region 702. The optical region 702 includes layered semiconductors between a bottom mirror 704 and a top mirror 706. The semiconductor layers form an active region 708 between the top mirror 706 and the bottom mirror 704. The active region 708 is a region having a material (active material) that is excited by energy added to the materials. The active region 708 includes a light-emitting region 712 between cladding layers 714. The exemplary laser device 700 is that of a Vertical-Cavity Surface-Emitting Laser ("VCSEL") device that emits coherent light through a window 716 in a top electrode 718. The bottom mirror 704 in this VCSEL example is a fully reflective mirror, while the top mirror 706 allows some light to transmit through the electrode window 716. Although a VCSEL device is shown, other arrangements, such as edge emitting semiconductor lasers, are within the scope of the disclosure.

The active region 708 includes a Ga alloy cladding, such as a combination of $In_{(1-x)}Ga_xAs_yP_{(1-y)}$, $Al_{(1-x)}Ga_xAs$, or $In_{(1-x)}As_xP$. In several examples, a substrate of InP or of GaAs may be used depending on the desired wavelength of the laser. Laser wavelength may be modified in GaAs substrates by adding N to $In_{(1-x)}Ga_xAl_yAs_{(1-x)}$ or $In_{(1-x)}Ga_xAl_yAs_{(1-y)}$ quantum dots.

The high-gain media devices described above may be formed as heterostructure devices with layered semiconductor construction. Depending on the desired downhole application and particular performance requirements, the heterostructure device may take on several forms. In several embodiments, a light array may be formed of several devices, where each device comprises a Quantum Well device, a Quantum Dot device, a Quantum Wire device, or a Quantum Dash device.

Having described above the several aspects of the disclosure, one skilled in the art will appreciate several particular embodiments useful in determining a property of an earth subsurface structure using a downhole spectrometer.

A downhole spectrometer in one particular embodiment includes a carrier conveyable into a well borehole that traverses a subterranean formation of interest, a plurality of semiconductor light sources disposed on the carrier, a fluid sample cell that receives light emitted from the plurality of semiconductor light sources, and at least one photodetector that detects light emitted from the plurality of semiconductor light sources and after the light interacts with a fluid in the fluid sample cell.

In another particular embodiment, a downhole spectrometer includes a plurality of semiconductor light sources that has one or more laser diodes. In another embodiment a plurality of semiconductor light sources in a downhole spectrometer has one or more light-emitting diodes (LEDs).

In another particular embodiment downhole spectrometer includes a plurality of semiconductor light sources, wherein each semiconductor light source emits a unique wavelength band. In one embodiment a downhole spectrometer has a photodetector that comprises a single photodetector having a response band at least as wide as an emitted bandwidth of from a plurality of semiconductor light sources.

In several particular embodiments, a downhole spectrometer includes a modulator that modulates the light emitted from a plurality of semiconductor light sources. In one embodiment the modulator modulates a temperature of the plurality of semiconductor light sources. In another embodiment, the modulator modulates temperature by changing an electrical current supplied to each light source in the plurality of semiconductor light sources. In another embodiment, the modulator modulates a light intensity of the plurality of semiconductor light sources. In other embodiments, the modulator modulates a wavelength of each light source of the plurality of semiconductor light sources, the modulator modulates an on-off cycle of each light source of the plurality of semiconductor light sources, and/or the modulator modulates a frequency of the plurality of slight sources.

In a particular embodiment, the frequency of each of the light sources in the plurality of semiconductor light sources is selected from relatively prime frequencies.

In a particular embodiment, a method for testing a formation using a downhole spectrometer includes conveying a carrier into a well borehole that traverses a subterranean formation of interest, emitting light from a plurality of semiconductor light sources disposed on the carrier, receiving the light at a fluid sample cell, and detecting the light emitted from the plurality of semiconductor light sources and after the light interacts with a fluid in the fluid sample cell using at least one photodetector.

In another particular embodiment, a method for testing a formation using a downhole spectrometer includes using a plurality of semiconductor light sources that has one or more laser diodes and emitting the light comprises emitting light at a plurality of narrow wavelengths. In one embodiment, a method includes using a plurality of semiconductor light sources that has one or more LEDs and emitting the light comprises emitting light at a plurality of wideband wavelengths.

One particular embodiment is a method that includes emitting light each semiconductor light source in a plurality of semiconductor light sources using a unique wavelength band.

In one embodiment, receiving light at a photodetector includes using a single photodetector having a response band at least a wide as an emitted bandwidth of from a plurality of semiconductor light sources.

In several particular embodiments, a method for testing a formation using a downhole spectrometer includes modulating light from the plurality of semiconductor light sources using a modulator. Modulating the light may include modulating a temperature of a plurality of semiconductor light sources and modulating the temperature may include changing an electrical current supplied to each light source or electrical current supplied to auxiliary resistive heaters in thermal contact with each light source in the plurality of semiconductor light sources. In one embodiment, modulating the light includes modulating a light intensity of the plurality of semiconductor light sources. Modulating the light may also include modulating a wavelength of each light source of the plurality of semiconductor light sources or modulating an on-off cycle of each light source of the plurality of semiconductor light sources. Modulating the light may also include modulating a frequency of the plurality of slight sources. The frequency of each of the light sources in the plurality of semiconductor light sources may be selected from relatively prime frequencies.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

Given the above disclosure of general concepts and specific embodiments, the scope of protection is defined by the claims appended hereto. The issued claims are not to be taken as limiting Applicant's right to claim disclosed, but not yet literally claimed subject matter by way of one or more further applications including those filed pursuant to the laws of the United States and/or international treaty.

What is claimed is:

1. A downhole formation testing spectrometer apparatus comprising:
    a carrier conveyable into a well borehole that traverses a subterranean formation of interest;
    a plurality of semiconductor light sources disposed on the carrier wherein each semiconductor light source in the plurality emits a unique wavelength band;
    a fluid sample cell that receives light emitted from the plurality of semiconductor light sources;
    at least one photodetector that detects light emitted from the plurality of semiconductor light sources and after the light interacts with a fluid in the fluid sample cell; and
    a modulator configured to modulate a light intensity of each of the semiconductor light sources in the plurality at a different electrical frequency and to filter output from the at least one photodetector to determine the spectral contribution from each of the semiconductor light sources.

2. An apparatus according to claim 1, wherein the plurality of semiconductor light sources includes one or more laser diodes.

3. An apparatus according to claim 1, wherein the plurality of semiconductor light sources includes one or more LEDs.

4. An apparatus according to claim 1, wherein the at least one photodetector comprises a single photodetector having a response band at least as wide as an emitted bandwidth of from the plurality of semiconductor light sources.

5. An apparatus according to claim 1, wherein the modulator further modulates a wavelength of each light source of the plurality of semiconductor light sources.

6. An apparatus according to claim 1, wherein the modulator modulates an on-off cycle of each light source of the plurality of semiconductor light sources to modulate the light intensity.

7. An apparatus according to claim 1, wherein the electrical frequency of modulation of each of the light sources in the plurality of semiconductor light sources is selected from relatively prime frequencies.

8. An apparatus according to claim 1, wherein the modulator further modulates a temperature of the plurality of semiconductor light sources.

9. An apparatus according to claim 1, wherein the plurality of semiconductor light sources include at least a first laser diode and a second laser diode, the apparatus further comprising a non-linear optical medium carrying light emitted from the first laser diode and the second laser diode to the fluid sample cell.

10. An apparatus according to claim 8, wherein the modulator modulates temperature by changing an electrical current supplied to each light source in the plurality of semiconductor light sources.

11. An apparatus according to claim 9, wherein the non-linear optical medium comprises an optic fiber, the first laser diode emitting a first light having a first short wavelength, the second laser diode emitting a second light having a second short wavelength, the first light and the second light being mixed and passed through the optic fiber to generate a third wavelength corresponding to a sum of the energies of the emitted first short wavelength and second short wavelength and a fourth wavelength corresponding to a difference between the energies of the emitted first short wavelength and second short wavelength.

12. An apparatus according to claim 11 wherein the fourth wavelength corresponds to an infrared wavelength range, the fourth wavelength being used to perform infrared spectroscopy.

13. A method for downhole spectrometry comprising:
conveying a carrier into a well borehole that traverses a subterranean formation of interest;
emitting light from a plurality of semiconductor light sources disposed on the carrier wherein each semiconductor light source in the plurality emits a unique wavelength band;
modulating an intensity of the light emitted from each semiconductor light source at a different electrical frequency using a modulator;
receiving the light at a fluid sample cell;
detecting the light emitted from the plurality of semiconductor light sources and after the light interacts with a fluid in the fluid sample cell using at least one photodetector; and
filtering the detected light to determine the spectral contribution from each of the semiconductor light sources.

14. A method according to claim 13, wherein the plurality of semiconductor light sources includes one or more laser diodes and emitting the light comprises emitting light at a plurality of narrow wavelengths.

15. A method according to claim 13, wherein plurality of semiconductor light sources includes one or more LEDs and emitting the light comprises emitting light at a plurality of wideband wavelengths.

16. A method according to claim 13, wherein receiving the light comprises using a single photodetector having a response band at least as wide as an emitted bandwidth from the plurality of semiconductor light sources.

17. A method according to claim 13, wherein modulating the light further includes modulating a wavelength of each light source of the plurality of semiconductor light sources.

18. A method according to claim 13, wherein modulating an intensity of the emitted light includes modulating an on-off cycle of each light source of the plurality of semiconductor light sources.

19. A method according to claim 13, wherein the frequency of each of the light sources in the plurality of semiconductor light sources is selected from relatively prime frequencies.

20. A method according to claim 13, wherein modulating further includes modulating a temperature of the plurality of semiconductor light sources.

21. A method according to claim 13, wherein emitting light comprises emitting light from a first laser diode and a second laser diode, the method further comprising passing the emitted light through a non-linear optical medium to the fluid sample cell.

22. A method according to claim 20, wherein modulating the temperature comprises changing an electrical current supplied to each light source in the plurality of semiconductor light sources.

23. A method according to claim 21, wherein the non-linear optical medium comprises an optic fiber and emitting light comprises emitting a first light having a first short wavelength from the first laser diode and emitting a second light having a second short wavelength from the second laser diode, the method further comprising mixing the first light and the second light forming a mixed light passed through the optic fiber.

24. A method according to claim 23 further comprising generating a third light wavelength corresponding to a sum of the energies of the emitted first short wavelength and second short wavelength, and generating a fourth wavelength corresponding to a difference between the energies of the emitted first short wavelength and second short wavelength.

25. A method according to claim 24, wherein the fourth wavelength corresponds to an infrared wavelength range, the method further comprising using the fourth wavelength to perform infrared spectroscopy.

* * * * *